United States Patent
Bode

(10) Patent No.: US 10,124,121 B2
(45) Date of Patent: Nov. 13, 2018

(54) SHEATH REMOVAL MECHANISM

(71) Applicant: Sanofi-Aventis Deutschland GMBH, Frankfurt am Main (DE)

(72) Inventor: Andreas Bode, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/111,653

(22) PCT Filed: Jan. 27, 2015

(86) PCT No.: PCT/EP2015/051596
§ 371 (c)(1),
(2) Date: Jul. 14, 2016

(87) PCT Pub. No.: WO2015/117864
PCT Pub. Date: Aug. 13, 2015

(65) Prior Publication Data
US 2016/0331908 A1 Nov. 17, 2016

(30) Foreign Application Priority Data
Feb. 4, 2014 (EP) .................................... 14153811

(51) Int. Cl.
*A61M 5/32* (2006.01)
*A61B 90/00* (2016.01)
(Continued)

(52) U.S. Cl.
CPC ........... *A61M 5/3204* (2013.01); *A61B 90/08* (2016.02); *A61M 5/20* (2013.01);
(Continued)

(58) Field of Classification Search
CPC .............. A61M 5/3202; A61M 5/3204; A61M 5/3269; A61M 5/3213; A61M 2005/3215;
(Continued)

(56) References Cited

U.S. PATENT DOCUMENTS 2,316,095 A * 4/1943 Mead, Jr. ................. A61M 5/24
604/209
5,067,949 A * 11/1991 Freundlich .......... A61M 5/3205
128/917
(Continued)

FOREIGN PATENT DOCUMENTS

| EP | 0747087 | 12/1996 |
| WO | WO2013/085454 | 6/2013 |
| WO | WO2013/164358 | 11/2013 |

OTHER PUBLICATIONS

International Search Report and Written Opinion in International Application No. PCT/EP2015/051596, dated Mar. 31, 2015, 10 pages.
(Continued)

*Primary Examiner* — Nathan R Price
*Assistant Examiner* — Melissa A Snyder
(74) *Attorney, Agent, or Firm* — Fish & Richardson P.C.

(57) ABSTRACT

Described is a sheath removal mechanism (1) for removing a protective needle sheath (2) from an injection needle (3) of a syringe (4) in a drug delivery device (5). The sheath removal mechanism (1) comprises a cap (6) adapted to cover a distal end of a drug delivery device (5) and adapted to engage the protective needle sheath (2), and at least one rotatable cam (7) adapted to move the cap (6) in a distal direction (D) away from the syringe (4) when rotated from a first rotational position (P1) towards a second rotational position (P2).

16 Claims, 3 Drawing Sheets

(51) Int. Cl.
*A61M 5/20* (2006.01)
*A61M 5/24* (2006.01)

(52) U.S. Cl.
CPC ............... *A61B 2090/0807* (2016.02); *A61B 2090/0814* (2016.02); *A61M 5/24* (2013.01); *A61M 5/3202* (2013.01)

(58) Field of Classification Search
CPC ........ A61M 5/3216; A61M 2005/3217; A61M 5/3219; B65D 41/02; B65D 41/026; B65D 41/06; B65D 51/18; B65D 47/244; B65D 47/266; B65D 50/04; B65D 50/061
See application file for complete search history.

(56) References Cited

U.S. PATENT DOCUMENTS

| | | | |
|---|---|---|---|
| 5,137,516 A | | 8/1992 | Rand et al. |
| 5,512,049 A | * | 4/1996 | Fallas ................. A61M 5/3213 604/192 |
| 5,584,818 A | * | 12/1996 | Morrison ............ A61M 5/3275 604/110 |
| 6,719,737 B2 | * | 4/2004 | Kobayashi .......... A61M 5/3216 206/365 |
| 7,201,736 B2 | * | 4/2007 | Hauri .................. A61M 5/3216 604/110 |
| 7,776,007 B2 | * | 8/2010 | Schuster ................ A61M 5/30 604/68 |
| 7,901,385 B2 | * | 3/2011 | Anderson ............. A61M 5/002 604/220 |
| 2009/0054849 A1 | * | 2/2009 | Burnell ............... A61M 5/2033 604/198 |

OTHER PUBLICATIONS

International Preliminary Report on Patentability in International Application No. PCT/EP2015/051596, dated Aug. 9, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

SHEATH REMOVAL MECHANISM

CROSS-REFERENCE TO RELATED APPLICATIONS

This application is a U.S. national stage application under 35 USC § 371 of International Application No. PCT/EP2015/051596, filed on Jan. 27, 2015, which claims priority to European Patent Application No. 14153811.6, filed on Feb. 4, 2014, the entire contents of which are incorporated herein by reference.

TECHNICAL FIELD

The invention relates to a sheath removal mechanism for removing a protective needle sheath from an injection needle of a syringe.

BACKGROUND OF THE INVENTION

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Usually the injection needle is equipped with a protective needle sheath for keeping the needle sterile and preventing it from being mechanically damaged. The protective needle sheath is attached to the needle when the auto-injector or the syringe is assembled. In order to prepare for an injection the user has to remove the protective needle sheath and is thus exposed to a high risk of needle stick injuries. Furthermore, removal of the protective needle sheath from the needle may require application of relatively high forces of up to 50 N.

There remains a need for an improved sheath removal mechanism.

SUMMARY OF THE INVENTION

Certain aspects of the disclosure can be implemented to provide an improved sheath removal mechanism.

Aspects of the disclosure are implemented by a sheath removal mechanism according to claim 1.

Exemplary embodiments of the invention are given in the dependent claims.

In an exemplary embodiment, a sheath removal mechanism for removing a protective needle sheath from an injection needle of a syringe in a drug delivery device comprises a cap adapted to cover a distal end of a drug delivery device and adapted to engage the protective needle sheath, and at least one rotatable cam adapted to move the cap in a distal direction away from the syringe when rotated from a first rotational position towards a second rotational position.

In an exemplary embodiment, the rotatable cam is pivoted in the cap and adapted to bear against a portion of the drug delivery device, in which the syringe is held.

In an exemplary embodiment, the rotatable cam is pivoted in a portion of the drug delivery device, in which the syringe is held, and the rotatable cam is adapted to bear against the cap.

In an exemplary embodiment, the rotatable cam is pivoted about a transversal axis transversally arranged with respect to a longitudinal axis of the protective needle sheath.

In an exemplary embodiment, at least one lever is arranged on the cam. The lever is U-shaped. The lever and the cam are integrally formed. The lever is directed in parallel with the longitudinal axis when in the first rotational position. The lever points in a proximal direction when in the first rotational position. A seal is arrangeable between the lever and a housing of the drug delivery device when the lever is in the first rotational position.

In an exemplary embodiment, the transversal axis is defined by at least one pin arranged on the cap or on the portion of the drug delivery device. The pin is integrally formed with the cap or the portion of the drug delivery device.

In an exemplary embodiment, a drug delivery device according to the present invention comprises a syringe with an injection needle and a protective needle sheath arranged over the needle, a portion adapted to retain the syringe within, and a sheath removal mechanism as described herein.

Due to the sheath removal mechanism the force which has to be exerted by a user for removing the protective needle sheath is considerably reduced. Furthermore, the sheath removal mechanism encourages the user to apply a purely linear force to the protective needle sheath when removing it thus preventing relative rotation between the protective needle sheath and the needle which may otherwise result in a blunt, bent or distorted needle or particles of the protective needle sheath being chipped away by the needle which may then inadvertently enter the lumen of the needle.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
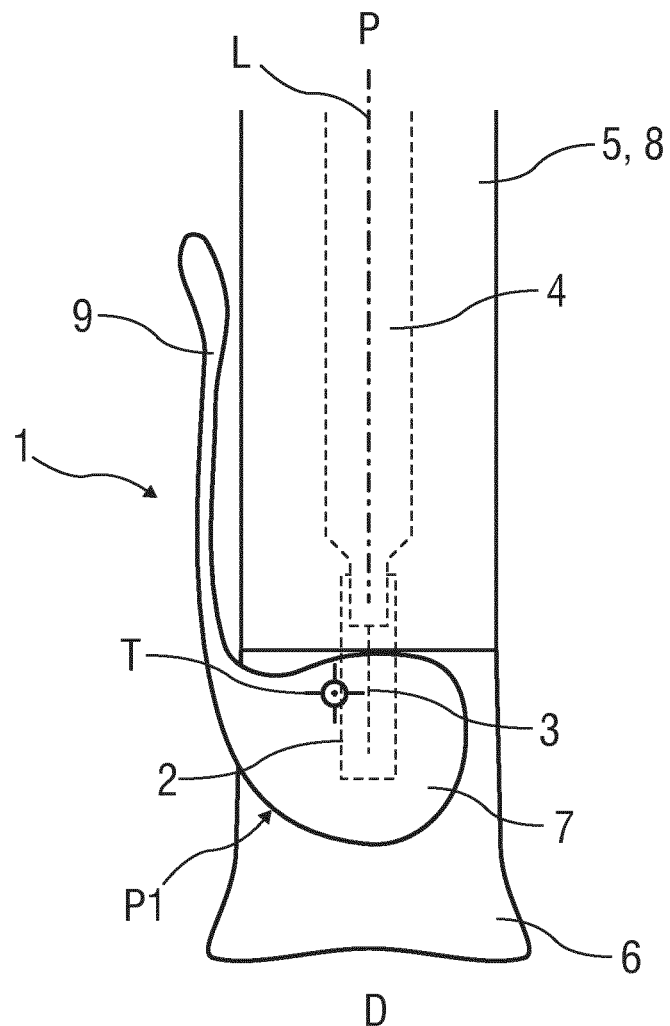
FIG. 1 is a schematic view of an exemplary embodiment of a sheath removal mechanism for removing a protective needle sheath from an injection needle of a syringe in a drug delivery device.

FIG. 1 is a schematic view of an exemplary embodiment of a sheath removal mechanism 1 for removing a protective needle sheath 2 from an injection needle 3 arranged or arrangeable on a syringe 4 or another medicament container in a drug delivery device 5. The sheath removal mechanism 1 comprises:

- a cap 6 adapted to cover a distal end of the drug delivery device 5 and adapted to engage the protective needle sheath 2, e.g. by a barb, a hook, a narrowed section, etc., such that the protective needle sheath 2 is coupled to the cap 6 and cannot move independently relative to the cap 6.

Figure 3:
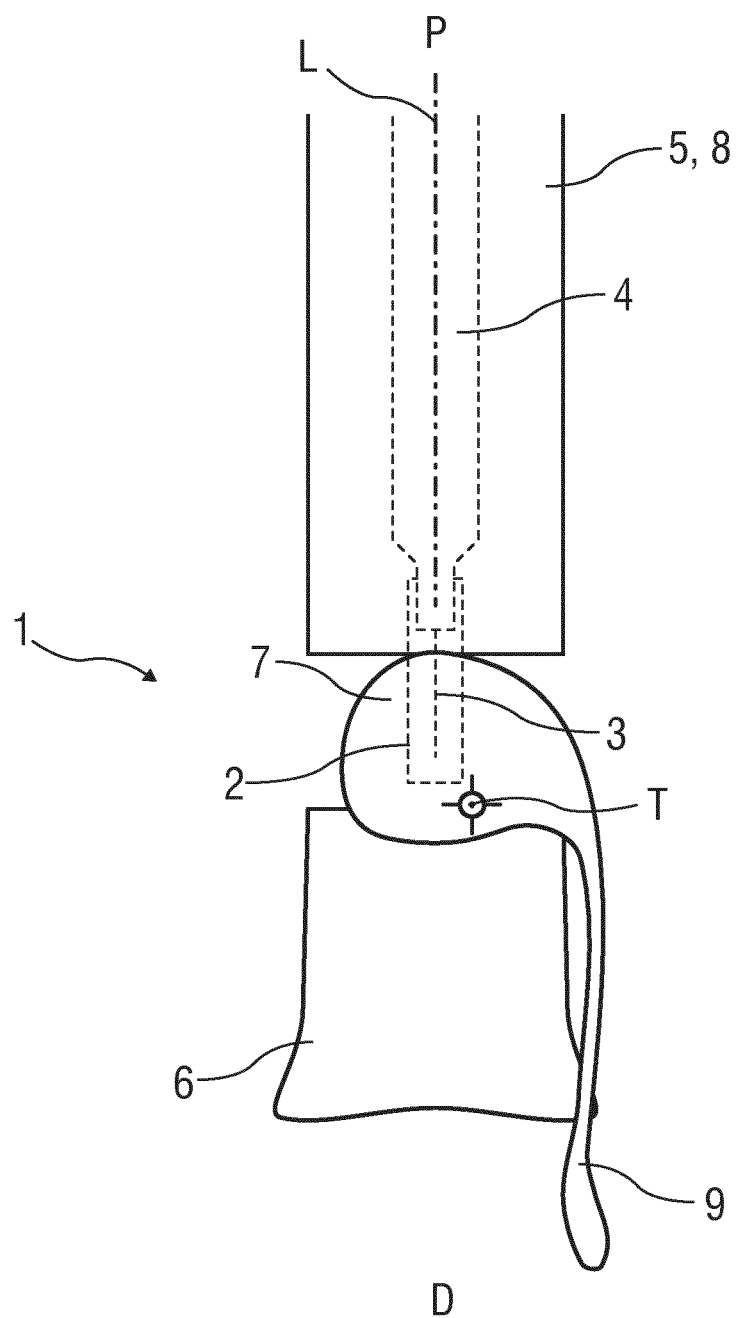
FIG. 3 is yet another schematic view of an exemplary embodiment of a sheath removal mechanism for removing a protective needle sheath from an injection needle of a syringe in a drug delivery device.

A rotatable cam 7 is arranged on the cap 6 such that the cap 6 is movable in a distal direction D away from the syringe 4 when the cam 7 is rotated from a first rotational position P1 as shown in FIG. 1 towards a second rotational position (cf. FIG. 3).

The rotatable cam 7 is pivoted in the cap 6 and adapted to bear against a portion of the drug delivery device 5, in which the syringe 4 is held. The portion of the drug delivery device 5 can be a housing 8 as in FIG. 1. In an alternative embodiment the portion of the drug delivery device 5 may be a syringe carrier (not illustrated) arranged within the housing 8.

The rotatable cam 7 is pivoted about a transversal axis T transversally arranged with respect to a longitudinal axis L of the protective needle sheath 2, the needle 3 and the syringe 4. The displacement of the cap 6 relative to the housing 8 is achieved by the cam 7 being eccentrically arranged about the transversal axis T.

In an exemplary embodiment a lever 9 is arranged on the cam 7 allowing the cam 7 to be easily rotated by a user.

Figure 2:
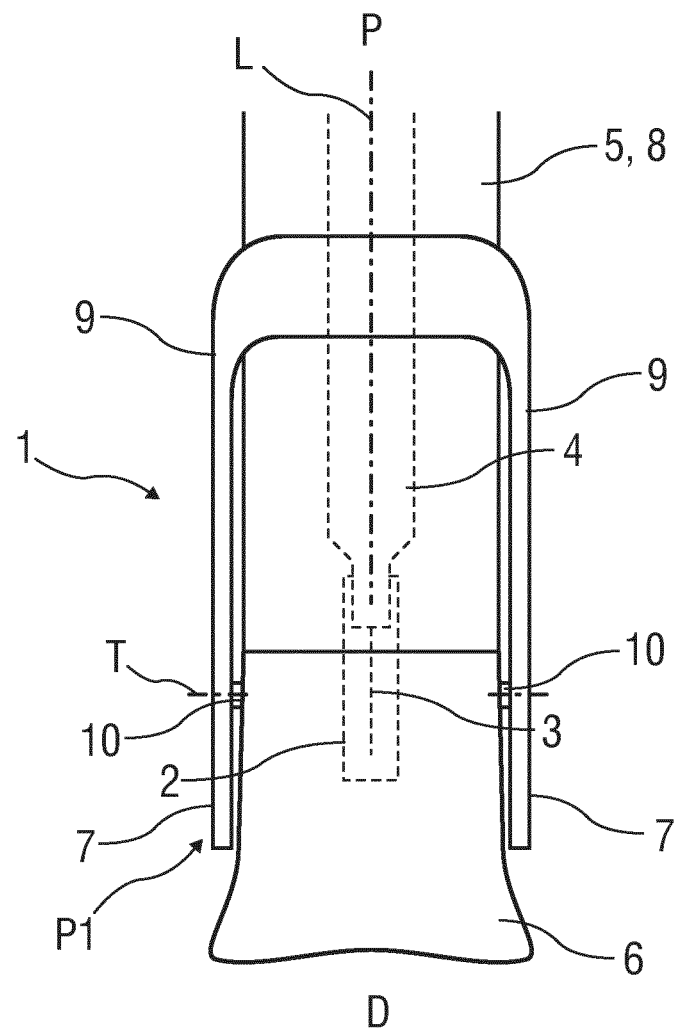
FIG. 2 is another schematic view of an exemplary embodiment of a sheath removal mechanism for removing a protective needle sheath from an injection needle of a syringe in a drug delivery device.

FIG. 2 is another schematic view of an exemplary embodiment of the sheath removal mechanism 1 from another perspective. FIG. 2 illustrates that two cams 7 are arranged opposite each other on the cap 6, each one connected to the lever 9 which substantially has a U-shape such that both cams 7 are rotated when the lever 9 is operated.

In an exemplary embodiment the lever 9 and the cams 7 are integrally formed thus minimizing the part count.

FIGS. 1 and 2 illustrate that the lever 9 is directed in parallel with the longitudinal axis L when in the first rotational position P1. In particular, the lever 9 points in a proximal direction P when in the first rotational position P1.

The transversal axis T is defined by one or more pins 10 arranged on the cap 6, wherein the pins 10 may be separate parts or be integrally formed with the cap 6 or with the cam 7 engaged in holes of the other one of the cap 6 and the cam 7. This way, the lever 9 and the cam 7 are the only additional parts when applied on a drug delivery device 5 such as an auto-injector thus minimizing the part count.

FIG. 3 is a schematic view of the sheath removal mechanism 1 with the cam 7 and lever 9 in a second rotational position P2. Starting from the first rotational position P1 the lever 9 has been pivoted such that the lever 9 is again arranged in parallel with the longitudinal axis L but points in the distal direction D. The eccentric cam 7 has been rotated about the transversal axis T. The relatively small radius of the cam 7 with respect to the transversal axis T of the first rotational position P1 has thus been increased such that the cap 6 is displaced in the distal direction D relative to the housing 8. As the syringe 4 is held in the housing 8 and the protective needle sheath 2 is held in the cap 6 the protective needle sheath 2 is removed from the syringe 4 and needle 3. Due to the cam 7 and the lever 9 the force which has to be exerted by a user for removing the protective needle sheath 2 is considerably reduced. The lever 9 encourages the user to apply a purely linear force to the protective needle sheath 2 when removing it thus preventing relative rotation between the protective needle sheath 2 and the needle 3 which may otherwise result in a blunt, bent or distorted needle 3 or particles of the protective needle sheath 2 being chipped away by the needle 3 which may then enter the lumen of the needle 3.

In an alternative exemplary embodiment the rotatable cam 7 may be pivoted in a portion of the drug delivery device 5 such as the housing 8 or a syringe carrier (not illustrated), wherein the rotatable cam 7 is adapted to bear against the cap 6.

In this case the transversal axis T would comprise at least one pin 10 arranged on the portion of the drug delivery device 5 in which the syringe 4 is held.

In an exemplary embodiment a seal may be arranged between or over the lever 9 and the housing 8 when the lever 9 is in the first rotational position P1 thus allowing differentiating an unused drug delivery device 5 from a used one or from a drug delivery device 5 which has been tampered with.

The invention claimed is:

1. A sheath removal mechanism for removing a protective needle sheath from an injection needle of a syringe in a drug delivery device, the sheath removal mechanism comprising:
    a cap adapted to cover a distal end of a drug delivery device and adapted to engage the protective needle sheath; and
    at least one rotatable cam adapted to bear against the cap to move the cap in a distal direction away from the syringe when the at least one rotatable cam is rotated from a first rotational position towards a second rotational position, wherein the at least one rotatable cam is adapted to pivot in a portion of the drug delivery device in which the syringe is held.

2. The sheath removal mechanism according to claim 1, wherein the at least one rotatable cam is adapted to pivot in the cap and adapted to bear against a portion of the drug delivery device in which the syringe is held.

3. The sheath removal mechanism according to claim 1, wherein at least one lever is arranged on the at least one rotatable cam.

4. The sheath removal mechanism according to claim 3, wherein the at least one lever is U-shaped.

5. The sheath removal mechanism according to claim 3, wherein the at least one lever and the at least one rotatable cam are integrally formed.

6. The sheath removal mechanism according claim 3, wherein the at least one lever is adapted to be directed in parallel with the longitudinal axis when in the first rotational position.

7. The sheath removal mechanism according to claim 6, wherein the at least one lever is adapted to point in a proximal direction when in the first rotational position.

8. The sheath removal mechanism according to claim 3, wherein a seal is arranged between the at least one lever and a housing of the drug delivery device when the at least one lever is in the first rotational position.

9. The sheath removal mechanism according to claim 1, further comprising at least one pin arranged on the cap or on the portion of the drug delivery device, wherein the transversal axis is defined by the at least one pin arranged on the cap or on the portion of the drug delivery device.

10. The sheath removal mechanism (1) according to claim 9, wherein the at least one pin is integrally formed with the cap or the portion of the drug delivery device.

11. A drug delivery device comprising:
   a syringe comprising:
      an injection needle, and
      a protective needle sheath arranged over the needle;
   a portion adapted to retain the syringe within the portion; and
   a sheath removal mechanism adapted to remove the protective needle sheath from the injection needle, the sheath removal mechanism comprising:
      a cap adapted to cover a distal end of a drug delivery device and adapted to engage the protective needle sheath; and
      at least one rotatable cam adapted to bear against the cap to move the cap in a distal direction away from the syringe when the at least one rotatable cam is rotated relative to the drug delivery device from a first rotational position towards a second rotational position about an axis that is perpendicular to a longitudinal axis of the cap.

12. The drug delivery device of claim 11, wherein the at least one rotatable cam is adapted to pivot in the cap and adapted to bear against a portion of the drug delivery device in which the syringe is held.

13. The drug delivery device of claim 11, wherein the at least one rotatable cam is adapted to pivot in a portion of the drug delivery device in which the syringe is held.

14. The drug delivery device of claim 11, wherein the at least one rotatable cam is adapted to pivot about a transversal axis transversally arranged with respect to a longitudinal axis of the protective needle sheath.

15. The drug delivery device of claim 11, wherein at least one lever is arranged on the at least one rotatable cam.

16. The drug delivery device of claim 15, wherein the at least one lever is U-shaped.

* * * * *

UNITED STATES PATENT AND TRADEMARK OFFICE
CERTIFICATE OF CORRECTION

PATENT NO. : 10,124,121 B2
APPLICATION NO. : 15/111653
DATED : November 13, 2018
INVENTOR(S) : Andreas Bode Page 1 of 1

It is certified that error appears in the above-identified patent and that said Letters Patent is hereby corrected as shown below:

In the Claims

Column 4, Line 59, Claim 6, after "according" insert -- to --

Column 5, Line 8, Claim 10, after "mechanism" delete "(1)"

Signed and Sealed this
Seventh Day of April, 2020

Andrei Iancu
*Director of the United States Patent and Trademark Office*